United States Patent [19]

Becker et al.

[11] Patent Number: 5,530,018

[45] Date of Patent: Jun. 25, 1996

[54] MESO-AZANORADAMANTANES

[75] Inventors: Daniel P. Becker, Glenview; Daniel L. Flynn, Mundelein; Clara I. Villamil, Glenview, all of Ill.

[73] Assignee: G. D. Searle & Co., Chicago, Ill.

[21] Appl. No.: 192,213

[22] Filed: Feb. 4, 1994

[51] Int. Cl.⁶ .......................... A61K 31/40; C07D 487/04
[52] U.S. Cl. ............................................. 514/411; 548/428
[58] Field of Search ............................. 548/428; 414/411

[56] References Cited

U.S. PATENT DOCUMENTS

| | | | |
|---|---|---|---|
| 5,137,893 | 8/1992 | Becker et al. | 514/293 |
| 5,196,547 | 3/1993 | Becker et al. | 548/453 |
| 5,219,850 | 6/1993 | Becker et al. | 514/214 |
| 5,227,377 | 7/1993 | Flynn et al. | 514/214 |
| 5,260,303 | 11/1993 | Becker et al. | 514/300 |
| 5,280,028 | 1/1994 | Flynn et al. | 514/294 |
| 5,280,029 | 1/1994 | Becker et al. | 514/300 |
| 5,354,757 | 10/1994 | Flynn et al. | 514/445 |

FOREIGN PATENT DOCUMENTS

| | | |
|---|---|---|
| 189002 | 7/1986 | European Pat. Off. . |
| 2152049 | 7/1985 | United Kingdom . |
| 2193633 | 2/1988 | United Kingdom . |
| 2231265 | 11/1990 | United Kingdom . |

OTHER PUBLICATIONS

Bick et al. "Aristofruticosine . . . ," Tetrahed. Lett., vol. 29, No. 27, pp. 3355–3356 (1988).
Bok et al. "3–Azanoradamantanes," Heterocycles, vol. 12, No. 3, pp. 343–347 (1979).
Beerli et al. "Synthesis of Aristotelia . . . ," Helv. Chim. Acta, vol. 74, pp. 110–116 (1991).

*Primary Examiner*—Jacqueline Haley
*Attorney, Agent, or Firm*—Cynthia S. Kovacevic; Roger A. Williams

[57] ABSTRACT

This invention relates to compounds of the formula:

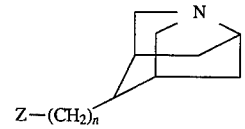

or a pharmaceutically acceptable salt thereof wherein Z is selected from the group consisting of

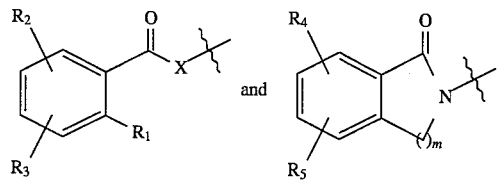

$R_1$ is alkoxy of one to six carbon atoms;

$R_2$, $R_3$, $R_4$ and $R_5$ are the same or different and are selected from the group consisting of hydrogen, halogen, $CF_3$, hydroxy, alkoxy of one to six carbon atoms, acyl of two to seven carbon atoms, amino, amino substituted by one or two alkyl groups of one to six carbon atoms, $C_2$–$C_7$ acylamino, aminocarbonyl, aminosulfonyl optionally substituted by one or two alkyl groups of one to six carbon atoms, $C_1$–$C_6$ alkylsulfonyl and nitro;

n is 0, 1 or 2;

m is 0 or 1;

X is O or $NR_7$; and $R_7$ is hydrogen or alkyl of 1 to 6 carbon atoms.

4 Claims, No Drawings

MESO-AZANORADAMANTANES

BACKGROUND OF THE INVENTION

The present invention relates to pharmaceutical agents (compounds) which act as 5-HT$_4$ agonists or antagonists and/or 5-HT$_3$ antagonists in mammals. As serotonin 5-HT$_4$ agonists, these compounds are gastrointestinal prokinetic agents useful for the treatment of human gastrointestinal (GI) hypomotility disorders such as reflux esophagitis, gastroparesis, nonulcer dyspepsia, ileus, constipation and irritable bowel syndrome (constipation predominant). As serotonin 5-HT$_4$ antagonists these compounds are useful in the treatment of motility disorders of the GI tract such as diarrhea and irritable bowel syndrome (diarrhea predominant). As serotonin 5-HT$_3$ antagonists these compounds are useful in slowing colonic transport and therefore are useful in the treatment of diarrhea predominant irritable bowel syndrome. The serotonin 5-HT$_4$ agonists or antagonists and/or serotonin 5-HT$_3$ antagonists are also useful in the treatment of emesis, anxiety, visceral pain, substance abuse (either cravings or withdrawal syndrome), cognitive disorders and other CNS disorders wherein treatment with a serotonin 5-HT$_4$ agonist or antagonist and/or serotonin 5-HT$_3$ antagonist would be indicated.

Serotonin (5-hydroxytryptamine; 5-HT) functions as a neurotransmitter in the mammalian central nervous system (CNS) and in the periphery. Serotonin is unsurpassed among monoamine neurotransmitters in the number of receptor subtypes identified. To date, the number of subtypes is into the teens, including the major subtypes 5-HT1A, 1B, 1C, 1D, 1E, 2A, 2B, 3 (perhaps subtypes), 1P, serotonin transporter, and more recently 5-HT$_4$ (vida infra). Because of the multiplicity of serotonin receptor subtypes, the identification of which serotonin receptor subtype is correlated to various physiological/pharmacological correlated to various physiological/pharmacological actions is complicated.

Serotonin has been known for some years to promote peristalsis in the GI tract in various animal models. During the mid 1980s, several specific antagonists to the 5-HT$_3$ receptor subtype were identified from independent laboratories. These 5-HT$_3$ antagonists were shown to be prokinetic in various rodent models. Hence, many publications and patents have issued wherein 5-HT$_3$ antagonists are claimed to be useful as GI prokinetic agents to treat various human hypomotility states: reflux esophagitis, nonulcer dyspepsia, gastroparesis, ileus, irritable bowel syndrome.

Gunning and Naylor (J. Pharm. Pharmacol. 1985, 37, 78) reported that metoclopramide (a 5-HT$_3$ antagonist which blocks the 5-HT$_3$ mediated Bezold Jarisch reflex) enhanced electrical-field stimulated contractions in guinea pig stomach strips. Simultaneously, Buchheit et al. (J. Pharm. Pharmacol. 1985, 37, 664) reported that three 5-HT$_3$ antagonists [metoclopramide, ICS-205930, and MDL 72222] both enhanced guinea pig stomach muscle strip contraction in vitro and led to increases in gastric emptying rates in vivo. H. Kimura et al. (Jpn. J. Pharmacol., 49 (suppl.) March 25-28, 1989, 196pp) independently reported that SN-307, a selective 5-HT$_3$ antagonist, enhanced transit of a charcoal meal in mice. J. S. Gidda et al. (Gastroenterology 1988, 95, A867) reported that several 5-HT$_3$ antagonists [ICS-205930, GR38032, and zacopride] enhanced gastric emptying. From these reports it was concluded that serotonin 5-HT$_3$ antagonists would be useful agents for the therapeutic treatment of human GI dysmotilities where restoration of peristalsis and enhancement of transit is indicated.

More recently several clinical reports indicate that 5-HT$_3$ antagonists do not accelerate GI transit in man. Talley et al. (Digestive Diseases and Sciences 1989, 34, 1511) has reported that GR38032, a selective 5-HT$_3$ antagonist, did not alter small intestinal transit times or mouth-to-cecum transit times. The conclusion was that GR38032 does not have a major effect on GI transit in man. Another clinical report by S. Gore et al. (Aliment. Pharmacol. Therap. 1990, 4, 139) has demonstrated that GR38032 not only failed to accelerate GI transit, but in fact slowed colonic transit in man. Thus while 5-HT$_3$ antagonists do accelerate GI transit in rodent species (guinea pig, mouse, rat), they do not affect small bowel transit in man, and decrease, rather than increase, colonic transit.

Canine models of GI transit may more accurately reflect human results. J. M. Van Nueten et al. (British J. Pharmacology, 1989, 96, 331P) reported recently that cisapride (a reported 5-HT$_3$ antagonist) enhanced antroduodenal motility in dogs, whereas ICS-205930, another potent 5-HT$_3$ antagonist did not. Moreover, ICS-205930 did not affect the responses to cisapride when the agents were coadministered. Nemeth and Gullikson (European J. Pharmacology, 1989, 166, 387) reported that the ability of BRL-24924 and cisapride to depolarize myenteric neurons was unrelated to their properties of 5-HT$_3$ antagonism.

The receptor mechanism by which cisapride, BRL-24924, metoclopramide, and other serotonergic agents are prokinetic is not related to their 5-HT$_3$ antagonist properties. The receptor mechanism responsible for their prokinetic activities is serotonergic, but at a different serotonin receptor subtype, presently referred to as 5-HT$_4$. (M. Tonini et al. Pharmacological Research, 1991, 24, 5).

Initially this clarification came from the laboratory of A. Dumuis, M. Sebben and J. Bockaert (Naunyn-Schmiedeberg's Arch. Pharmacol., 1989, 340, 403). The prokinetic activity of a variety of benzamides, including cisapride and BRL-24924, were found to correlate with agonist activity at a novel 5-HT$_4$ receptor subtype identified in mouse embryonic colliculi neurons. Shortly thereafter, D. Craig and D. Clarke identified the 5-HT$_4$ receptor in the myenteric plexus of the guinea pig ileum (J. Pharmacol. Exp. Ther., 1990, 252, 1378). Quite recently Craig and Clarke also demonstrated that the peristaltic reflex evoked by serotonin and the benzamide BRL-24924 (renzapride) was mediated through agonism at 5-HT$_4$ receptors.

The natural product aristofruiticosine which contains an azanoradamantane nucleus is discussed in *Tetra. Lett.*, 1988, 29, 3355 and *Helv. Chem. Acta.*, 991, 74, 110.

An azanoradamantane nucleus substituted with nitriles or carboxyl groups is reported in *Heterocycles*, 1979, 12, 343.

There is a need in the area of serotonin regulation for agents with broad clinical usefulness. Serotonin is one of the newer neurotransmitters to be recognized for physiological importance and agents which interact with 5-HT receptors are currently the focus of much research. P. Bonate, *Clinical Neuropharmacology*, Vol. 14, No. 1, pp. 1–16 (1991).

Accordingly, it is the object of this invention to produce compounds for use as pharmaceutical agents which will exhibit 5-HT$_4$ serotonin agonist or antagonist and/or 5-HT$_3$ serotonin antagonist activity in mammals. The compounds of the present invention meet the need for an agent which has broad clinical usefulness for treating conditions affected by 5-HT$_4$ agonists or antagonists and/or 5-HT$_3$ antagonists in mammals by administering therapeutically effective amounts of the compounds.

SUMMARY OF THE INVENTION

This invention relates to compounds of the formula I

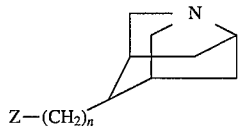  (I)

or a pharmaceutically acceptable salt thereof wherein Z is selected from the group consisting of

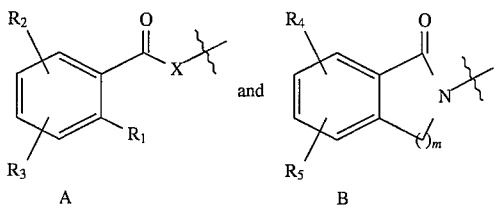

$R_1$ is alkoxy of one to six carbon atoms;

$R_2$, $R_3$, $R_4$ and $R_5$ are the same or different and are selected from the group consisting of hydrogen, halogen, $CF_3$, hydroxy, alkoxy of one to six carbon atoms, acyl of two to seven carbon atoms, amino, amino substituted by one or two alkyl groups of one to six carbon atoms, $C_2$–$C_7$ acylamino, aminocarbonyl, aminosulfonyl optionally substituted by one or two alkyl groups of one to six carbon atoms, $C_1$–$C_6$ alkylsulfonyl and nitro;

n is 0,1 or 2;

m is 1 or 2;

X is O or $NR_7$; and $R_7$ is hydrogen or alkyl of one to six carbon atoms.

The present invention also provides pharmaceutical compositions comprised of a therapeutically effective amount of a compound of Formula I in combination with a pharmaceutically acceptable carrier and methods for treating conditions responsive to 5-$HT_4$ serotonin agonists or antagonists and/or 5-$HT_3$ serotonin antagonists.

DETAILED DESCRIPTION OF THE INVENTION

This invention encompasses compounds of the Formula I as previously described.

Within the class of compounds defined by Formula I, there is a sub-class of preferred compounds represented by the formula II:

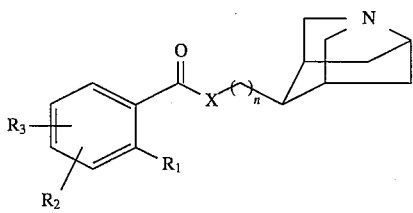  (II)

or a pharmaceutically acceptable salt thereof wherein $R_1$ is alkoxy of one to six carbon atoms;

$R_2$ and $R_3$ are the same or different and are selected from the group consisting of hydrogen, halogen, $CF_3$, hydroxy, alkoxy of one to six carbon atoms, acyl of two to seven carbon atoms, amino, amino substituted by one or two alkyl groups of one to six carbon atoms, $C_2$–$C_7$ acylamino, aminocarbonyl, aminosulfonyl optionally substituted by one or two alkyl groups of one to six carbon atoms, $C_1$–$C_6$ alkylsulfonyl and nitro;

n is 0, 1 or 2; and

X is NH.

Included within the preferred subclass of compounds of the Formula II are:

syn-4-(acetylamino)-5-chloro-N-(hexahydro-2,6-methano-1H-pyrrolizin-8-yl)-2-methoxybenzamide, monohydrochloride;

anti-4-(acetylamino)-5-chloro-N-(hexahydro-2,6-methano-1H-pyrrolizin-8-yl)-2-methoxybenzamide;

syn-4-amino-5-chloro-N-(hexahydro-2,6-methano-1H-pyrrolizin-8-yl)-2-methoxybenzamide;

syn-4-amino-5-chloro-N-(hexahydro-2,6-methan1H-pyrrolizin-8-yl)-2-methoxybenzamide, hydrochloride;

anti-4-amino-5-chloro-N-(hexahydro-2,6methano-1H-pyrrolizin-8-yl)-2-methoxybenzamide;

anti-4-amino-5-chloro-N-(hexahydro-2,6methano-1H-pyrrolizin-8-yl)-2-methoxybenzamide, monohydrochloride;

4-(acetylamino)-5-chloro-N-(hexahydro-2,6-methano1H-pyrrolizin-8-ylmethyl)-2-methoxybenzamide, hydrochloride;

4-amino-5-chloro-N-(hexahydro-2,6-methano-1H-pyrrolizin-8-ylmethyl)-2-methoxybenzamide;

4-amino-5-chloro-N-(hexahydro-2,6-methano-1H-pyrrolizin-8-ylmethyl)-2-methoxybenzamide, monohydrochloride;

anti-4-amino-5-chloro-N-(hexahydro-2,6-methano-1H-pyrrolizin-8-ylmethyl)-2-methoxybenzamide, monohydrochloride; or syn-4-amino-5-chloro-N-(hexahydro-2,6-methano-1H-pyrrolizin-8-ylmethyl)-2-methoxybenzamide, monohydrochloride.

Another sub-class of preferred compounds is represented by the formula III:

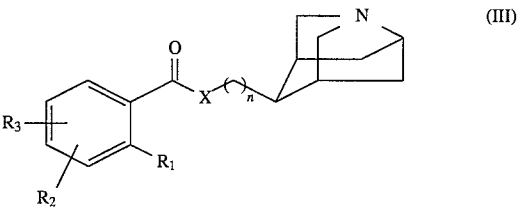  (III)

or a pharmaceutically acceptable salt thereof wherein $R_1$ is alkoxy of one to six carbon atoms;

$R_2$ and $R_3$ are the same or different and are selected from the group consisting of hydrogen, halogen, $CF_3$, hydroxy, alkoxy of one to six carbon atoms, acyl of two to seven carbon atoms, amino, amino substituted by one or two alkyl groups of one to six carbon atoms, $C_2$–$C_7$ acylamino, aminocarbonyl, aminosulfonyl optionally substituted by one or two alkyl groups of one to six carbon atoms, $C_1C_6$ alkylsulfonyl and nitro;

n is 0, 1 or 2; and

X is O.

Included within this preferred subclass of compounds of the Formula III is:

(hexahydro-2,6-methano-1H-pyrrolizin-8-yl) 4-amino-5-chloro-2-methoxybenzoate.

Included within the classes and subclasses of compounds embraced by Formulas I–III are the pharmaceutically acceptable salts of such compounds.

In the structures herein a bond drawn across a bond in a ring indicates that the bond can be to any available atom of the ring structure.

The term "pharmaceutically acceptable salt," as used herein, refers to conventionally accepted pharmaceutical salts prepared by processes which are well known to those of ordinary skill in the art. [See for example, S M. Berge, et al , . "Pharmaceutical Salts," *J. Pharm. Sci.*, 66:1–19 (1977)].

The term "composition" as used herein means a product which results from the mixing or combining of more than one element or ingredient.

The term "pharmaceutically acceptable carrier" as used herein means a pharmaceutically-acceptable material, composition or vehicle, such as a liquid or solid filler, diluent, excipient, solvent or encapsulating material, involved in carrying, formulating, or transporting a chemical agent.

The term "therapeutically effective amount" shall mean that amount of drug or pharmaceutical agent that will elicit the biological or medical response of a tissue, system or animal (mammal) that is being sought by a researcher or clinician.

The term "alkyl" as used herein means a univalent hydrocarbon radical having from one to six carbon atoms and derived by the removal of a single hydrogen atom from a straight or branched chain saturated hydrocarbon. Representative of such radicals are methyl, ethyl, n-propyl, isopropyl, n-butyl, sec-butyl, isobutyl, tert-butyl, n-octyl, 2,4-dimethylpentyl and the like.

The term "alkoxy" as used herein means an alkyl radical, as defined above having one or more oxygen atoms attached thereto. Representative alkoxy groups include methoxy, ethoxy, propoxy, tert-butoxy and the like.

The term "halogen" or "halo" as used herein means a fluoro, chloro, bromo or iodo radical.

The term "amino" as used herein is represented by the radical —$NR_8R_9$ wherein $R_8$ and $R_9$ are independently hydrogen or an alkyl group as previously described.

The term "acylamino" as used herein is represented by the radical

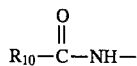

wherein $R_{10}$ is an alkyl group of one to six carbon atoms as defined above.

The term "aminosulfonyl" as used herein is represented by the radical $R_{11}R_{12}N—SO_2—$ wherein $R_{11}$ and $R_{12}$ are independently hydrogen or an alkyl group as defined above.

The term "aminocarbonyl" as used herein is represented by the radical

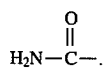

The term "acyl" as used herein means a radical of the formula

wherein $R_{13}$ is an alkyl group as defined above.

The term "alkylsulfonyl is represented by the radical $R_{14}—SO_2—$ wherein $R_{14}$ is an alkyl group as defined above.

The compounds herein exhibit 5-$HT_4$ agonism or antagonism and/or 5-$HT_3$ antagonism. The 5-$HT_3$ activity possessed by the compounds of this invention was determined by the radioligand receptor binding assay as described herein. 5-$HT_4$ agonist activity was determined in the in vitro rat tunica muscularis mucosae (TMM) assay described herein. (Baxter et al., Naunyn Schmied Arch. Pharmacol, 1991, 343, 439). Similarly, use of the rat TMM assay may be employed to identify 5-$HT_4$ antagonists which block the action of serotonin. One with skill in the art could determine the activity of the compounds of the present invention using the methodology of these assays, described herein, without undue experimentation.

The compounds of the invention having X=NH and the phthalimidines exhibit 5-$HT_4$ agonist activity which is associated with the planar conformation of the molecules. The benzamide compounds are forced into a planar conformation via internal hydrogen bonding. The other compounds of the invention exhibit 5-$HT_4$ activity which on a continuum can be antagonist activity or mixed or partial agonist/antagonist activity.

By virtue of their activity as 5-$HT_4$ agonists or antagonists and/or 5-$HT_4$ antagonists the compounds of Formula I–III are useful in treating conditions such as gastrointestinal motility disorders, emesis, anxiety, cognitive disorders and other CNS disorders. As used herein gastrointestinal motility disorders responsive to treatment with 5-$HT_4$ agonists include reflux esophagitis, non-ulcer dyspepsia, gastroparesis, ileus, irritable bowel syndrome (constipation predominant), constipation, and the like. As used herein gastrointestinal motility disorders responsive to treatment with 5-$HT_4$ antagonists include diarrhea, irritable bowel syndrome (diarrhea predominant) and the like. As used herein disorders responsive to 5-$HT_3$ antagonists include emesis due to either cancer chemotherapy or operative procedures, anxiety, cognitive disorders, drug abuse (either cravings or withdrawal syndrome), irritable bowel syndrome (diarrhea predominant) and the like. A physician or veterinarian of ordinary skill can readily determine whether a subject exhibits such a condition treatable with a 5-$HT_4$ agonist or antagonist or 5-$HT_3$ antagonist.

The compounds of the present invention can be administered in such oral dosage forms as tablets, capsules, softgels, pills, powders, granules, elixirs or syrups. The compounds can also be administered intravascularly, intraperitoneally, subcutaneously, intramuscularly or topically, using forms known in the pharmaceutical art. In general, the preferred form of administration is oral.

For the orally administered pharmaceutical compositions and methods of the present invention, the foregoing active ingredients will typically be administered in admixture with suitable pharmaceutical diluents, excipients or carriers (collectively referred to hereinafter as "carrier" materials). Such carrier materials are suitably selected with respect to the intended form of administration and consistent with conventional pharmaceutical practices.

For example, for oral administration in the form of tablets or capsules, a therapeutically effective amount of one or more compounds of the present invention can be combined with any oral pharmaceutically acceptable inert carrier such as lactose, starch, sucrose, cellulose, magnesium stearate, calcium sulfate and the like or various combinations thereof. For oral administration in liquid forms, such as in softgels, elixirs, syrups and the like, a therapeutically effective amount of the active drug components can be combined with any oral pharmaceutically acceptable inert carrier such as water, ethanol, polyethylene glycol, vegetable oils, propylene glycol, benzylalcohol and the like or various combinations thereof.

When desired or necessary, suitable binders, lubricants, disintegrating agents, preservatives, and coloring or flavoring agents can also be incorporated into the mixture. Suitable binders include starch, gelatin, natural sugars, corn sweeteners, natural and synthetic gums and waxes and the like, or combinations thereof. Lubricants can include boric acid, sodium benzoate, sodium acetate, sodium chloride and the like, or combinations thereof. Disintegrators include without limitation starch, methylcellulose, agar, bentonite, guar gum and the like, or combinations thereof.

For intravascular, intraperitoneal, subcutaneous or intramuscular administration, one or more compounds of the present invention can be combined with a suitable carrier such as water, saline, aqueous dextrose and the like. For topical administration therapeutically effective amounts of one or more compounds of the present invention can be combined with pharmaceutically acceptable creams, oils, waxes, gels and the like.

Regardless of the route of administration selected, a therapeutically effective amount of the compounds of the present invention are formulated into pharmaceutically acceptable dosage forms by conventional methods known to those skilled in the art. The dosages for preventing or treating conditions mediated by 5-HT$_4$ agonists or antagonists and/or 5-HT$_3$ antagonists with the compounds of the present invention is determined in accordance with a variety of factors, including the type, age, weight, sex and medical condition of patient, the severity of the condition, the route of administration and the particular compound employed in the treatment. A physician or veterinarian of ordinary skill can readily determine and prescribe the effective amount of drug required to prevent or arrest progress of the condition. In so proceeding, the physician or veterinarian could employ relatively low doses at first and subsequently increase the dose until a maximum response is obtained. The daily doses of the compounds of the invention are ordinarily in the range of about 1 to 1000 mg, more preferably in the range of about 10 to 500 mg.

The compounds of this invention are generally prepared according to reaction schemes I–V.

Chemical Preparation:

The known hexahydro-2,6-methano-1H-pyrrolizin-8-one 1 [T. R. Bok and W. N. Speckamp, *Heterocycles* 12, 343 (1979)] is utilized as shown in scheme I for the preparation of syn-hexahydro-2,6-methano-1H-pyrrolizin8-ol 2 and anti-hexahydro-2,6-methano-1H-pyrrolizin8-ol 2 by reducing 1 with sodium borohydride in methanol or with lithium aluminum hydride (LAH) in tetrahydrofuran (THF). Alternatively, reduction with sodium/alcohol mixtures affords a different ratio of the alcohols 2 and 3. The mixture of 2 and 3 is separated by silica gel chromatography.

The ketone 1 is also used to prepare the syn-hexahydro-2,6-methano-1H-pyrrolizin-8-amine 4 and the anti-hexahydro-2,6-methano-1H-pyrrolizin-8-amine 5 by conversion to its oxime derivative, followed by reduction with lithium aluminum hydride (LAH) to give the primary amines ($R_7$=H). Alternatively, reaction of primary amine with ketone 1 under conditions of reductive amination afford the secondary amines 4 and 5 wherein $R_7$ is alkyl.

In compounds where n is I (see formula II), the ketone 1 is reacted with tosylmethylisocyanide in the presence of base (preferably potassium t-butoxide) to afford the separable nitriles 6 and 7. (See Scheme II.) These nitriles are individually reduced with lithium aluminum hydride in tetrahydrofuran to afford the syn-hexahydro-2,6-methano-1H-pyrrolizin-8methylamine and the anti-hexahydro-2,6-methano-1H-pyrrolizin-8-methylamine 9, respectively. Alternatively, the nitriles 6 and 7 are converted to their respective methyl esters 10 and 11 (methanol, HCl), which are then reduced with lithium aluminum hydride in an etheral solvent (preferably tetrahydrofuran) to give syn-hexahydro-2,6-methano-1H-pyrrolizin-8-methylcarbinol 12 and the anti-hexahydro2,6-methano-1H-pyrrolizin-8-methylcarbinol 13, respectively.

Scheme III illustrates the preparation of substituted azanoradamantanes wherein n is 2 (see formula II). The methylcarbinols 12 and 13 are separately converted into intermediates wherein the alcohol functionality is a leaving group (e.g. tosylate). These tosylates are reacted with sodium cyanide in a polar aprotic solvent (dimethylformamide) to afford the syn- and anti- cyanomethyl substituted compounds 14 and 15, respectively. Treatment of 14 and 15 individually with lithium aluminum hydride in an etheral solvent gives rise to the desired syn-hexahydro-2,6-methano-1H-pyrrolizin-8-ethanamine 16 and the anti-hexahydro-2,6-methano-1H-pyrrolizin-8-ethanamine 17. Alternatively, conversion of the nitriles 14 and 15 into their respective methyl esters as described above, followed by reduction with lithium aluminum hydride in an etheral solvent affords syn-hexahydro-2,6-methano-1H-pyrrolizin-8-ethanol 18 and the anti-hexahydro-2,6-methano-1H-pyrrolizin-8-ethanol 19.

Scheme IV illustrates the coupling of substituted benzoic acids (C) with the appropriate amine or alcohol to afford compounds of formulae II. Typical acid-activating reagents (acid chloride, DCC (1,3-dicyclohexylcarbodiimide), ECDI [1-(3-dimethylaminopropyl)-3-ethylcarbodiimide hydrochloride], CDI (1,1'-carbonyldiimidazole), etc.) are suitable for this coupling. Preferably CDI is used as the acid-activating reagent, with the coupling reaction being performed in dimethylformamide (DMF) or tetrahydrofuran or a similar polar aprotic solvent. For the couplings involving alcohols (MX=HO), preferably the alcohol is converted to a metallated alkoxide by use of an inorganic base such as sodium, potassium or cesium carbonate or alternatively sodium or potassium hydride.

Scheme V illustrates the process used to afford the phthalimidine compounds of formula IV. In Scheme V, Q1 and Q2 are independently leaving groups (e.g. chloride) or taken together are oxygen, m is 1 or 2, and $R_4$ and $R_5$ are as described above. Compounds of formulae D [AU 8207867 p. 14], are reacted with amines in an inert solvent such as toluene, tetrahydrofuran, or dimethylformamide optionally in the presence of base such as potassium carbonate or cesium carbonate to afford the desired compounds of the formula IV.

SCHEME I

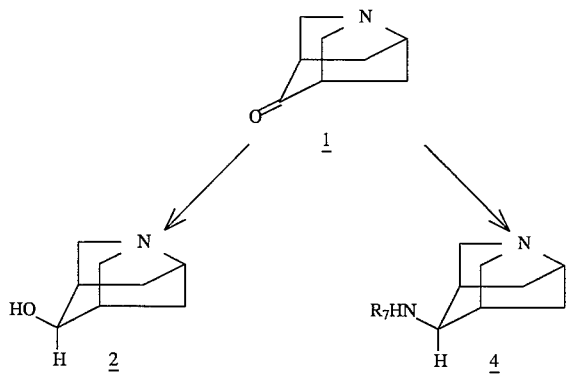

5,530,018
9
-continued
SCHEME I
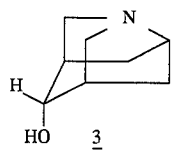
3
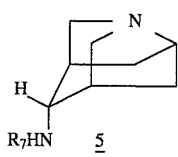
5
SCHEME II
1
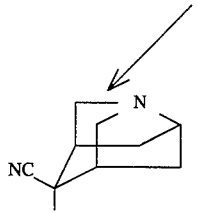
6
7
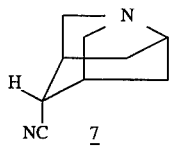
10
11
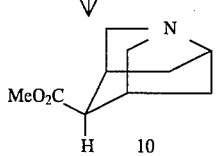
8
9
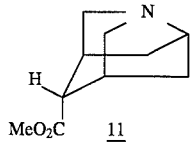
12
13
SCHEME III
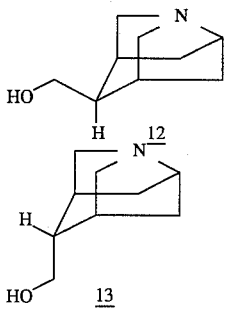
13
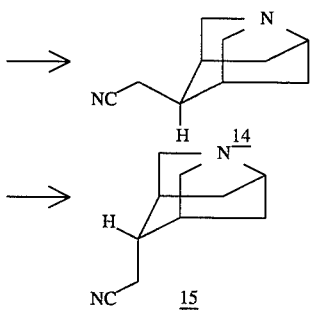
14
15
10
-continued
SCHEME III
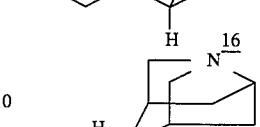
16
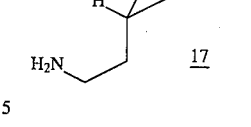
17
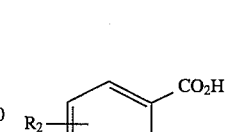
18
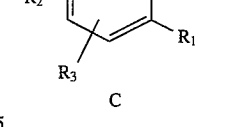
19
SCHEME IV
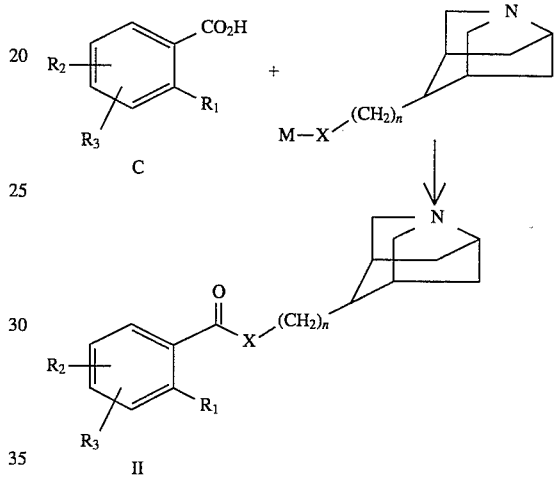
II
MX = HR$_7$N (for Examples 1, 2, 7, 10, 12)
MX = HO or metallated alkoxide (for Example 13)
SCHEME V
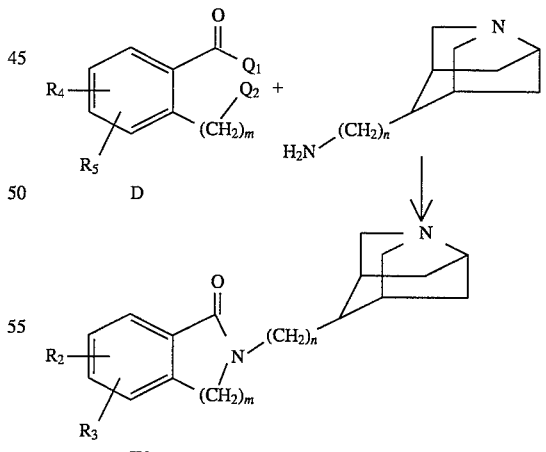
IV

EXAMPLE A

Hexahydro-8-[(phenylmethoxy) imino]-2,6-methano-1H-pyrrolizine

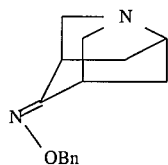

Hexahydro-2,6-methano-1H-pyrrolizin-8-one (1.45 g, 10.99 mmol) prepared by the method of Speckamp [Tetrahedron 27, 3143, (1971)] was dissolved in a 1:1 solution of pyridine/ethanol (20 ml). O-Benzyl hydroxylamine hydrochloride (1.85 g, 11.6 mmol) was added and the solution was stirred for 20 hours at room temperature. Removal of the solvents in vacuo afforded a solid which was purified by chromatography on silica gel eluting with 10% MeOH $(NH_3)/CHCl_3$ to give the title compound (1.1 g, 41%).

Calculated for $C_{15}H_{18}N_2O * 0.25 H_2O$:

|   | Calc | Found |
|---|------|-------|
| C | 72.99 | 73.12 |
| H | 7.55 | 7.47 |
| N | 11.35 | 11.44 |

Calculated MS for $C_{15}H_{18}N_2O$: 242.1419
Found: 242.1392

EXAMPLE B

Anti-hexahydro-2,6-methano-1H-pyrrolizin-8-amine and Syn-hexahydro-2,6-methano-1H-pyrrolizin-8-amine

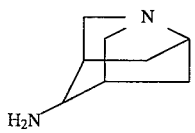

Hexahydro-8-[(phenylmethoxy) imino]-2,6-methano-1H-pyrrolizine of Example A (600 mg, 2.5 mmol), was dissolved in t-amyl alcohol (40 ml). Sodium metal (740 mg, 32.0 mmol) was added to the solution and the contents heated under reflux for 7 hours. Water (20 ml) was added to the reaction mixture, which was then acidified with 1N HCl to pH 2.0. The solution was evaporated to dryness, water (10 ml) was added and the solution was basified with 1N NaOH to pH 14.0. The aqueous solution was extracted with $CHCl_3$, the combined extracts were dried over $MgSO_4$ and evaporated to dryness to give the title compounds as a mixture of epimers (320 mg, 94%).

EXAMPLES 1 AND 2

Syn-4,(acetylamino)-5-chloro-N-(hexahydro-2,6-methano-1H-pyrrolizin8-yl)-2-methoxybenzamide and Anti-4-(acetylamino)-5-chloro-N-(hexahydro-2,6-methano-1H-pyrrolizin-8-yl)-2-methoxybenzamide

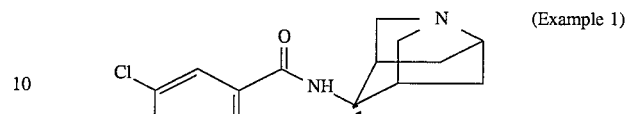
(Example 1)

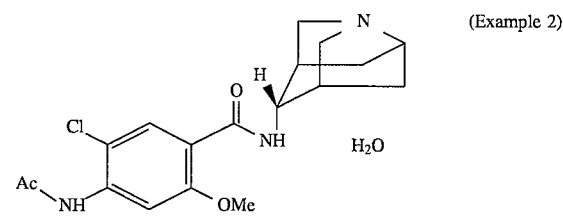
(Example 2)

4-Acetylamino-5-chloro-2-methoxybenzoic acid [prepared according to the procedure described in JP 61218581] (1.02 g, 4.2 mmol) and 1,1-carbonyl diimidazole (CDI) (680 mg, 4.2 mmol) were dissolved in 10 ml of dimethylformamide (DMF) and stirred for 0.5 hour. The amine mixture from Example B (580 mg, 4.2 mmol) was then dissolved in DMF (1 ml) and added to the above solution. This solution was stirred for 12 hours at room temperature and then concentrated to dryness. The residue was dissolved in $CHCl_3$ and washed successively with 15% $K_2CO_3$ and $H_2O$ and dried over $MgSO_4$. Concentration gave an oil which was purified by chromatography (prep-plate) eluting with 10% MeOH $(NH_3)/CHCl_3$ (3 elutions) to give the syn title compound (245 mg) and the anti title compound (180 mg)

Syn isomer as the monohydrochloride salt:
Analysis calculated for $C_{18}H_{22}N_3O_3Cl * HCl * 9/10 H_2O$:

|   | Calc | Found |
|---|------|-------|
| C | 51.91 | 51.68 |
| H | 6.00 | 6.02 |
| N | 10.09 | 10.04 |
| Cl | 17.02 | 17.39 |

MS calculated for $C_{18}H_{22}N_3O_3Cl$: 363.1349
Found: 363.1331
Anti isomer: Analysis calculated for $C_{18}H_{22}N_3O_3Cl * H_2O$:

|   | Calc | Found |
|---|------|-------|
| C | 56.62 | 56.66 |

-continued

|   | Calc  | Found |
|---|-------|-------|
| H | 6.33  | 6.17  |
| N | 11.00 | 10.55 |
| Cl| 9.28  | 9.42  |

MS calculated for $C_{18}H_{22}N_3O_3Cl$:
Found: 363.1363

EXAMPLE 3

Syn-4-amino-5-chloro-N-(hexahydro,2,6-methano-1H-pyrrolizin-8-yl)-2-methoxybenzamide

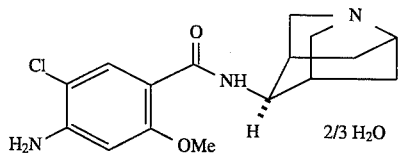

2/3 H₂O

To a solution of syn-4-(acetylamino)-5-chloro-N-(hexahydro-2,6-methano-1H-pyrrolizin-8-ylmethyl)-2-methoxybenzamide of Example 1 (162 mg, 0.445 mmol) in ethanol (3 ml) was added potassium hydroxide (50 mg, 0.890 mmol) and the reaction was heated under reflux for 1.5 hours. The reaction was evaporated to dryness and the residue was purified by chromatography on silica gel eluting with 10% MeOH (NH₃)/CHCl₃ to give the title compound (99 mg, 69%).

Analysis calculated for $C_{16}H_{20}N_3O_2Cl * 2/3 \; H_2O$:

|   | Calc  | Found |
|---|-------|-------|
| C | 57.57 | 57.12 |
| H | 6.44  | 6.20  |
| N | 12.59 | 12.16 |

MS calculated for $C_{16}H_{20}N_3O_2Cl$: 321.1239
Found: 321.1234

EXAMPLE 4

Syn-4-amino-5-chloro-N-(hexahydro-2,6-methano-1H-pyrrolizin-8-yl)-2-methoxybenzamide, hydrochloride

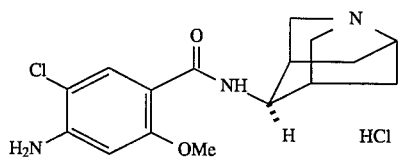

HCl

The hydrochloride salt of Example 3 was prepared by dissolving the free base (62 mg, 0.170 mmol) in a solution of HCl in MeOH [prepared by the addition of acetyl chloride (0.012 ml, 0.170 mmol) to MeOH (0.5 ml)], and concentrating the solution to dryness to afford the title compound (52 mg, 80%).

Analysis calculated for $C_{16}H_{20}N_3O_2Cl * 1.1 \; HCl * 1.5 \; H_2O$:

|    | Calc  | Found |
|----|-------|-------|
| C  | 49.41 | 49.36 |
| H  | 6.25  | 6.04  |
| N  | 10.80 | 10.39 |
| Cl | 19.14 | 19.10 |

MS calculated for $C_{16}H_{20}N_3O_2Cl$: 321.1239
Found: 321.1225

EXAMPLE 5

Anti-4-amino-5-chloro-N-(hexahydro-2,6-methano-1H-pyrrolizin-8-yl)-2-methoxybenzamide

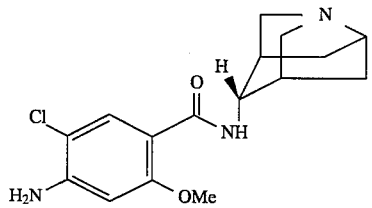

To a solution of anti-4-(acetylamino)-5-chloro-N-(hexahydro-2,6-methano-1H-pyrrolizin-8-yl)-2-methoxybenzamide of Example 2 (41 mg, 0.113 mmol) in ethanol (3 ml) was added potassium hydroxide (6.3 mg, 0.113 mmol) and the resulting solution was heated under reflux for 45 minutes. After concentration to dryness, the residue was purified by chromatography on silica gel eluting with 20% MeOH (NH₃)/CHCl₃ to give the title compound (24 mg, 67%).

Analysis calculated for $C_{16}H_{20}N_3O_2Cl * 1/3 \; H_2O$:

|   | Calc  | Found |
|---|-------|-------|
| C | 58.62 | 59.02 |
| H | 6.35  | 6.55  |
| N | 12.81 | 12.39 |

MS calculated for $C_{16}H_{20}N_3O_2Cl$: 321.1243
Found: 321.1243

EXAMPLE 6

Anti-4-amino-5-chloro-N-(hexahydro-2,6-methano-1H-pyrrolizin-8-yl)-2-methoxybenzamide, monohydrochloride

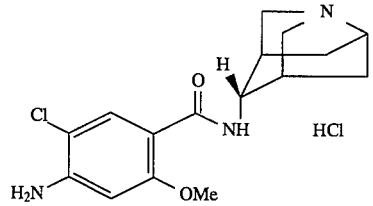

HCl

The hydrochloride salt of Example 5 was prepared by dissolving the title compound of Example 5 (110 mg, 0.302 mmol) in a solution of methanolic HCl [prepared by addition of acetyl chloride (0.014 ml, 0.302 mmol) to MeOH (0.5 ml)], and concentrating the solution to dryness to afford an oil. The oil was dissolved in MeOH and added dropwise to solution diethyl ether. Filtration gave the title compound as a colorless powder (54 mg, 50%).

Analysis calculated for $C_{16}H_{20}N_3O_2Cl \cdot HCl \cdot \frac{2}{3} H_2O$:

|   | Calc  | Found |
|---|-------|-------|
| C | 51.90 | 51.99 |
| H | 6.08  | 5.94  |
| N | 11.08 | 11.01 |
| Cl| 19.15 | 18.92 |

MS calculated for $C_{16}H_{20}N_3O_2Cl$: 321.1243
Found: 321.1236

EXAMPLE C

Syn-hexahydro-2,6-methano-1H-pyrrolizine-8-carbonitrile (C,1) and Anti-hexahydro-2,6-methano-1H-pyrrolizine-8-carbonitrile (C-2)

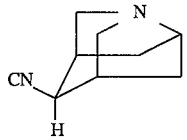

To a solution of hexahydro-2,6-methano-1H-pyrrolizin-8-one (1.95 g, 14.2 mmol), tosylmethyl isocyanide (3.6 g, 18.5 mmol) and ethanol (1.67 ml, 28.4 mmol) in ethylene glycol dimethyl ether (30 ml) (DME) at 0° C. was added potassium t-butoxide (3.80 g, 33.8 mmol). The reaction mixture was stirred for 2 hours at room temperature followed by 2 hours at 45° C. The suspension was then filtered and the filtrate was concentrated to dryness. To the residue was added brine (40 ml) and the mixture was extracted with CHCl₃. The organic layer was dried over MgSO₄, filtered and concentrated to dryness. The resulting oil was purified by chromatography on silica gel, eluting with 10% MeOH (NH₃)/CHCl₃ to give the syn isomer (231 mg, 10.9%) followed by elution of the anti isomer (270 mg, 12.8%).

syn-isomer (C-1):

$^1$H NMR (300 MHz, CDCl₃) δ 1.82 (2H, dd, J=2.5, 12.5 Hz); 2.02 (2H, m) 2.49 (2H, s); 2.85 (1H, m); 2.94 (2H, d, J=12 Hz); 3.35 (2H, dd, J=2.5, 12 Hz); 3.74 (1H, t, J=7 Hz). $^{13}$C NMR (75 MHz, CDCl₃) δ 33.3, 39.2, 41.6, 59.4, 63.5, 120.5.

Anti-isomer (C-2):

$^1$H NMR (300 MHz, CDCl₃) δ 2.01 (2H, m) ; 2.19 (2H, br d, J=2.5, 12.5 Hz); 2.55 (2H, br s); 3.05 (2H, br d); 3.08 (1H, m); 3.11 (2H, dd, J=2.0 Hz); 3.87 (1H, s, J=7.2 Hz). $^{13}$C NMR (75 MHz, CDCl₃) δ 33.4, 38.9, 40.0, 60.6, 64.9, 120.5.

EXAMPLE D

Hexahydro-2,6-methano-1H-pyrrolizin-8-methanamine

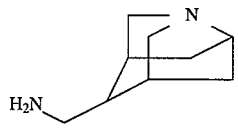

To the mixture of syn and anti nitriles of Example C (147 mg, 0,966 mmol) in THF (3 ml) was added a solution of 1M LAH in THF (2 ml, 1.93 mmol) at room temperature. This mixture was heated to reflux for one hour. The reaction mixture was then cooled to room temperature and 0,073 ml of water was added to quench the excess lithium aluminum hydride. This was followed by the addition of a solution of 0,073 ml of 15% NaOH and an additional 0.22 ml of water. The resulting mixture was filtered and the solid was washed well with THF. Concentration of the filtrate gave the desired compounds as a mixture (147 mg, 100%).

EXAMPLE 7

4-(Acetylamino)-5-chloro-N-(hexahydro-2,6-methano-1H-pyrrolizin-8-ylmethyl)-2-methoxybenzamide, hydrochloride

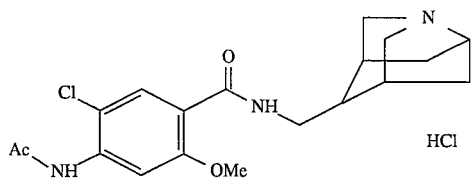

4-Acetylamino-5-chloro-2-methoxybenzoic acid (235 mg, 0.965 mmol) and CDI (156 mg, 0.965 mmol) were dissolved in 5 ml of DMF and stirred for 0.5 hour. A solution of the amines of Example D (147 mg, 0.956 mmol) in 1 ml DMF was then added to the above solution. This mixture was stirred for 10 hours and concentrated to dryness. The residue was dissolved in CHCl₃, washed successively with water and 10% K₂CO₃ and then dried over K₂CO₃, filtered and concentrated to dryness. The resulting solid was chromatographed with silica gel eluting with 15% MeOH (NH₃)/CHCl₃ to give a 51% (anti)/49%(syn) epimeric mixture of the title compound (196 mg, 54%). Conversion to the hydrochloride salt was accomplished by treatment with methanolic HCl.

Analysis calculated for $C_{19}H_{24}N_3O_3Cl \cdot 1.1\ HCl \cdot .25\ H_2O$:

|   | Calc  | Found |
|---|-------|-------|
| C | 54.02 | 53.67 |
| H | 6.11  | 5.76  |
| N | 9.95  | 9.62  |
| Cl| 17.65 | 17.85 |

MS calculated for $C_{19}H_{24}N_3O_3Cl$:
Found: 377.1506

EXAMPLE 8

4-Amino-5-chloro-N-(hexahydro-2,6-methano-1H-pyrrolizin-8-ylmethyl)-2-methoxybenzamide

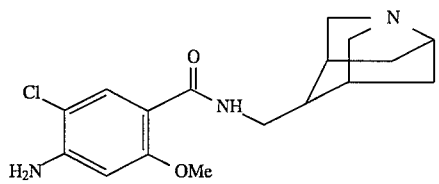

To a solution of the title compound of Example 7 (121 mg, 0.320 mmol) in ethanol (10 ml) was added potassium hydroxide (36 mg, 0.640 mmol) and the resulting solution was heated under reflux for 1 hour. After concentration to dryness the residue was purified by chromatography on silica gel eluting with 10% MeOH (NH$_3$)/CHCl$_3$ to give the title compound as an epimeric mixture (86 mg, 80%).

Analysis calculated for $C_{17}H_{22}N_3O_2Cl*2/3$ H$_2$O:

|   | Calc  | Found |
|---|-------|-------|
| C | 58.96 | 58.70 |
| H | 6.55  | 6.76  |
| N | 11.77 | 12.08 |

MS calculated for $C_{17}H_{22}N_3O_2Cl$:
Found: 335.1377

EXAMPLE 9

4-Amino-5-chloro-N-(hexahydro,2,6-methano-1H-pyrrolizin-8-ylmethyl)-2-methoxybenzamide, monohydrochloride

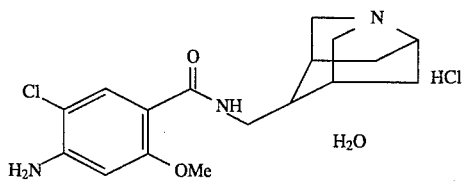

The hydrochloride salt was prepared by dissolving the free base of Example 8 in a solution of methanolic HCl, [prepared by addition of acetyl chloride (0.016 ml, 0.220 mmol) in MeOH (0.5 ml)] and concentrating the resulting solution to dryness to afford the title compound as a mixture of epimers (44 mg, 59%).

MS calculated for $C_{17}H_{22}N_3O_2Cl$:
Found: 335.1402

EXAMPLE E

Anti-hexahydro-2,6-methano-1H-pyrrolizin-8-yl-methanamine

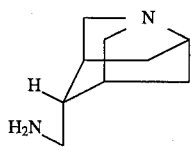

To a solution of the anti nitrile of Example C-2 (250 mg, 1.67 mmol) in THF (3 ml) was added a solution of 1M LAH in THF (5 ml, 5.0 mmol) at room temperature. This mixture was heated under reflux for 1 hour. The reaction mixture was then cooled to room temperature and 0.19 ml of water was added to quench the excess LAH. This was followed by the addition of 0.19 ml of 15% NaOH and an additional 0.58 ml of water. The resulting mixture was filtered and the solid was washed well with THF. Concentration of the filtrate gave the desired compound as an oil (190 mg, 75%).

$^1$H NMR (300 MHz, CDCl$_3$) δ 1.70 (2H, m); 1.80 (2H, dd, J=7.0, 12.5 Hz); 1.86 (2H, m); 2.14 (2H, s); 2.70 (2H, d, J=7.5 Hz); 2.92 (2H, distorted d, J=12.0 Hz); 3.58 (1H, t, J=7.0 Hz).

$^{13}$C NMR (75 MHz, CDCl$_3$): δ 38.6, 38.6, 44.6, 45.3, 60.8, 6.6.

EXAMPLE 10

Anti-4-Acetylamino-5-chloro-N-(hexahydro-2,6-methano-1H-pyrrolizin-8-ylmethyl)-2-methoxybenzamide

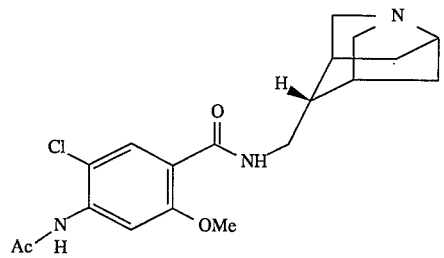

To a solution of 4-acetylamino-5-chloro-2methoxybenzoic acid (304 mg, 1.25 mmol) in DMF (5 ml) was added CDI (202 mg, 1.25 mmol) in DMF. After stirring for 0.5 hour the anti amine of Example E (190 mg, 1.25 mmol) was dissolved in 1 ml DMF and added to the above solution. This mixture was stirred for 10 hours and then concentrated to dryness. The residue was dissolved in CHCl$_3$, washed successively with water and 10% K$_2$CO$_3$ and then dried over K$_2$CO$_3$, filtered and concentrated to dryness. The resulting solid was purified by chromatography on silica gel eluting with 15% MeOH (NH$_3$)/CHCl$_3$ to give the title compound as an oil (273 mg, 58%).

MS calculated for $C_{19}H_{24}N_3O_3Cl$: 377.1506
Found: 377.1512

EXAMPLE 11

Anti-4-amino-5-chloro-N-(hexahydro-2,6-methano-1H-pyrrolizin-8-ylmethyl)-2-methoxybenzamide, monohydrochloride

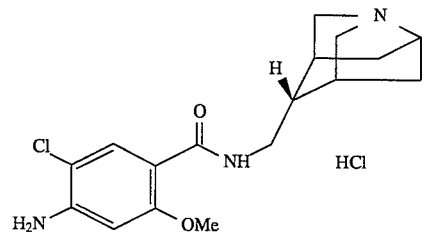

To a solution of the compound of Example 10 (178 mg, 0.471 mmol) in ethanol (5 ml) was added potassium hydroxide (53 mg, 0.942 mmol) and the reaction was heated under reflux for 1 hour. The solution was evaporated to dryness and the resulting residue was purified by silica gel eluting with 10% MeOH (NH$_3$)/CHCl$_3$ to give an oil (69 mg, 44%). The oil was dissolved in methanolic HCl prepared from the addition of acetyl chloride (0.016 ml, 0.205 mmol) to MeOH], and concentrated to dryness to afford the title compound (58 mg, 33%).

Analysis calculated for $C_{17}H_{22}N_3O_2Cl*HCl*1.1$ H$_2$O:

|   | Calc  | Found |
|---|-------|-------|
| C | 52.08 | 51.73 |
| H | 6.22  | 6.40  |

|   | Calc  | Found |
|---|-------|-------|
| N | 10.72 | 10.54 |

MS calculated for $C_{17}H_{22}N_3O_2Cl$: 335.1400
Found: 335.1400

EXAMPLE F

Syn-Hexahydro-2,6-methano-1H-pyrrolizine-8-methanamine

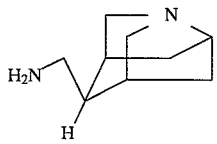

A solution of the syn nitrile of Example C-1 (104 mg, 0.702 mmol) in THF (2.5 ml) was added to a refluxing solution of 1M LAH in THF (2.1 ml, 2.1 mmol) dropwise over 0.5 hour. This mixture was heated under reflux for an additional 1 hour. The reaction mixture was cooled and a solution of 0.08 ml of water in 1 ml THF was added to quench the excess LAH. This was followed by 0.08 ml of 15% NaOH and an additional 0.24 ml of water. The resulting mixture was filtered and the solid was washed with THF. Concentration of the filtrate gave the title compound as an oil (101 mg, 94%).

$^1$H NMR (300 MHz, CDCl$_3$) δ 1.68 (2H, m); 1.88 (2H, dd, J=2.5, 7.5 Hz), 1.92 (2H, m); 2.10 (2H, br s); 2.71 (2H, distorted d, J=12 Hz); 2.84 (2H, d, J=7.5 Hz); 3.05 (2H, dd J=2.5, 12.0 Hz); 3.65 (1H, t, J=7.0 Hz).

$^{13}$C NMR (75 MHz, CDCl$_3$) 6 38.7, 42.9, 44.7, 45.6, 60.2, 62.7.

MS calculated for $C_9H_{16}N_2$: 152.1313
Found: 152.1313

EXAMPLE 12

Syn-4-acetylamino-5-chloro-N-(hexahydro-2,6-methano-1H-pyrrolizin-8-ylmethyl)-2-methoxybenzamide

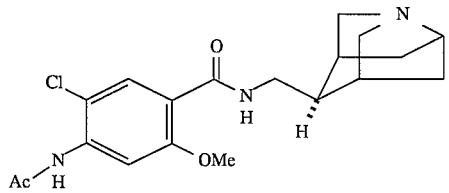

4-Acetylamino-5-chloro-2-methoxybenzoic acid (160 mg, 0.657 mmol) and CDI (108 mg, 0.657 mmol) were dissolved in 2 ml of DMF and stirred for 0.5 hour. The syn amine of Example F (100 mg, 0.657 mmol) was then dissolved in DMF (1 ml) and added to the above solution. This mixture was stirred for 10 hours and then concentrated to dryness. The residue was dissolved in CHCl$_3$, washed successively with water and 10% K$_2$CO$_3$ and dried over K$_2$CO$_3$, filtered and concentrated to dryness. The oil was purified by chromatography on silica gel eluting with 15% MeOH (NH$_3$)/CHCl$_3$ to give the title compound (45 mg, 19%).

$^1$H NMR (300 MHz, CDCl$_3$) δ 1.80 (2H, m); 1.96 (3H, m), 2.12 (2H, m); 2.29 (3H, s); 2.81 (2H, d); 3.22 (2H, dd); 3.60 (2H, q); 3.72 (1H, t), 3.89 (3H, s), 7.86 (2H, m), 8.21 (1H, s), 8.32 (1H, s).

$^{13}$C NMR (75 MHz, CDCl$_3$) δ 25.1, 38.5, 41.9, 42.1, 42.5, 6.5, 60.2, 62.3, 62.3, 103.9, 114.2, 117.3, 132.0, 38.0, 156.6, 163.8, 168.7.

EXAMPLE 13

(Hexahydro-2,6-methano-1H-pyrrolizin-8-yl) 4-amino-5-chloro-2-methoxybenzoate

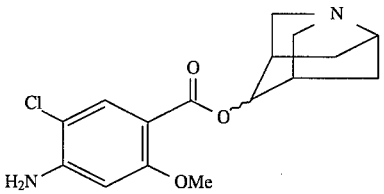

4-Amino-5-chloro-2-methoxybenzoic acid (323 mg, 1.6 mmol) and CDI (260 mg, 1.6 mmol) were dissolved in 3 ml of DMF and stirred for 0.5 hour at room temperature. Separately, a solution of hexahydro-2,6-methano-1H-pyrrolizine-8-ol (mixture of endo and exo) prepared according to the procedure of Speckamp [*Tetrahedron* 1971, 27, 3143] in DMF (2.5 mL) was added to a suspension of sodium hydride (63 mg, 1.6 mmol) in DMF (1 mL) and the suspension was stirred at room temperature for 0.5 hour. This suspension was then added to the above-described solution of CDI in DMF cooled at 0° C. The reaction was then stirred at room temperature for 2.5 hours and then concentrated to dryness. To the residue was then added water (10 ml) and the mixture was extracted with CHCl$_3$ to give (3X). The combined extracts were washed with brine, dried over MgSO$_4$, filtered and concentrated to dryness. The oil was purified via preparative thin-layer chromatography eluting with 10% CH$_3$OH (NH$_3$)/CHCl$_3$ to give an epimeric mixture (50:50 endo:exo by HPLC) of the title compound (70 mg, 14%) as the free base.

Analysis calculated for $C_{16}H_{19}N_2O_3Cl*55\ H_2O$:

|   | Calc  | Found |
|---|-------|-------|
| C | 57.76 | 57.42 |
| H | 6.09  | 5.66  |
| N | 8.42  | 7.97  |

MS calculated for $C_{16}H_{19}N_2O_3Cl$: 377.1086
Found: 377.1081

The hydrochloride salt was prepared by dissolving the free base (71 mg, 0.22 mmol) in a solution of methanolic HCl [prepared by addition of acetyl chloride (0.016 ml, 0.220 mmol) to MeOH (0.5 ml)] and concentrating the solution to dryness to afford an oil. The oil was dissolved in MeOH and added dropwise to Et$_2$O with rapid stirring. Filtration of the resulting solid gave the title compound as a solid (63 mg, 80%).

Analysis calculated for $C_{16}H_{19}N_2O_3Cl*.9\ HCl*.6\ H_2O$:

|   | Calc  | Found |
|---|-------|-------|
| C | 52.45 | 52.06 |
| H | 5.80  | 5.61  |
| N | 7.65  | 7.27  |

|      | Calc  | Found |
| ---- | ----- | ----- |
| Cl   | 18.38 | 17.97 |

MS calculated for $C_{16}H_{19}N_2O_3Cl$: 377.1086
Found: 377.1092

EXAMPLE 14

Syn-4-amino-5-chloro-N-(hexahydro-2,6-methano-1H-pyrrolizin-8-ylmethyl)-2-methoxybenzamide, monohydrochloride

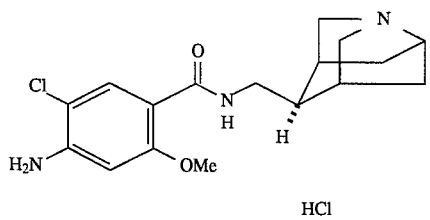

HCl

To a solution of the compound of Example 12 (33 mg, 0.087 mmol) in ethanol (1 ml) was added potassium hydroxide (10 mg, 0.18 mmol) and the reaction was heated under reflux for 1.5 hours. The solution was evaporated to dryness and the resulting residue was purified by preparative thin-layer chromatography eluting with 5% MeOH (NH$_3$)/CHCl$_3$ to give the desired compound as the free base (22 mg, 44%). The free base was dissolved in methanolic HCl [prepared from the addition of acetyl chloride (0.0046 ml, 0.065 mmol) to MeOH (1 ml)], and concentrated to dryness to afford a residue. Crystallization from Et$_2$O/methanol gave the title compound (15 mg) as a colorless solid.

Analysis calculated for $C_{17}H_{22}N_3O_2Cl*HCl*H_2O$:

|   | Calc  | Found |
| - | ----- | ----- |
| C | 52.31 | 52.75 |
| H | 6.46  | 6.66  |
| N | 10.77 | 10.66 |

MS calculated for $C_{17}H_{22}N_3O_2Cl$: 335.1400
Found: 335.1398

A. In Vitro Functional Assay for Serotonin 5-HT$_4$ agonism: RAT TMM

Serotonin 5-HT$_4$ agonism was measured in the rat esophagus in vitro preparation as reported by Baxter et al. [Naunyn. Schmied. Arch. Pharmacol. 343, 439 (1991)]. Agonist activity was determined utilizing relaxation of carbachol-contracted rat tunica muscularis mucosae (TMM). One 2 cm segment of intrathoracic esophagus proximal to the diaphragm was removed from male rats, weighing approximately 300 gm, and the outer muscle layers removed. The inner tunica muscularis mucosa was mounted under 0.2–0.3 g of tension in a tissue bath containing oxygenated Tyrode's solution at 37° C. Cortisterone acetate (30 µM) and fluoxetine (1 µM) were included in the buffer to prevent uptake of serotonin, as well as pargyline (10 µM) to inhibit monoamine oxidase. Following a 30 minute equilibrium period, tissues were isometrically contracted with carbachol (3 µM) to obtain a tonic contraction. A stable plateau was obtained within 20 minutes when test compound was added cumulatively to relax the muscle strip. EC$_{50}$ values were obtained for each agonist in tissues from 5 rats. EC$_{50}$ values for agonists at this 5-HT$_4$ receptor are indicated in Table I.

TABLE I

| Compound   | 5-HT$_4$ Agonism (Rat TMM) In Vitro Assay: EC50 values |
| ---------- | ----------- |
| Serotonin  | 9 nM        |
| Example 1  | 3335 nM     |
| Example 2  | >10,000 nM  |
| Example 3  | 2229 nM     |
| Example 4  | 711.6 nM    |
| Example 5  | 705.5 nM    |
| Example 6  | 382.0 nM    |
| Example 7  | ≧10,000 nM  |
| Example 9  | 397 nM      |
| Example 11 | 660 nM      |
| Example 13 | 216.3 nM    |
| Example 14 | 420.7 nM    |
| Cisapride  | 55 nM       | b. Serotonin (5-HT$_3$)

Procedure: GR65630 binds to the 5-HT$_3$ receptor. Brain cortices were obtained from male rats and a membrane fraction prepared by standard techniques. 0.04 mg of membrane prep was incubated with 0.2 nM [$^3$H]-GR65630 for 66 minutes at 22° C. Non-specific binding was estimated in the presence of 1 uM ICS 205,930. Membranes were filtered and washed 3 times and the filters were counted to determine [$^3$H]-GR65630 specifically bound. [Kilpatrick GJ, Jones BJ and Tyers MB, Identification and Distribution of 5-HT$_3$ Receptors in Rat Brain Using Radioligand Binding Assay, Nature 330, 746–748 (1987)].

Results: $K_d$=2.46 $B_{max}$=154 fmol/mg protein % Specific Binding: 70

TABLE II

Effect of Compounds on [H]-GR65630 Bound (0.2 nM)

| Compound   | Ki       |
| ---------- | -------- |
| Cisapride  | 1500 nM  |
| Quipazine  | 0.18 nM  |
| ICS 205,930| 0.51 nM  |
| 5-HT       | 0.39 uM  |
| Example 4  | 22.0 nM  |
| Example 6  | 3.8 nM   |
| Example 14 | 1.1 nM   |

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. The compound syn-4-amino-5-chloro-N-(hexahydro-2, 6-methano-1H-pyrrolizin-8-ylmethyl)-2-methoxybenzamide or a pharmaceutically acceptable salt thereof.

2. A pharmaceutical composition comprising a therapeutically effective amount of the compound syn-4-amino-5-chloro-N-(hexahydro-2,6-methano-1H-pyrrolizin-8-ylmethyl)-2-methoxybenzamide or a pharmaceutically acceptable salt thereof; and a pharmaceutically acceptable carrier.

3. A method of treating conditions responsive to 5-HT$_4$ agonists comprising administering to a mammal in need of such treatment a therapeutically effective amount of the compound syn-4-amino-5-chloro-N-(hexahydro-2,6-methano-1H-pyrrolizin-8-ylmethyl)-2-methoxybenzamide or a pharmaceutically acceptable salt thereof.

4. A method of treating conditions responsive to 5-HT$_3$ antagonists comprising administering to a mammal in need of such treatment a therapeutically effective amount of the compound syn-4-amino-5-chloro-N-(hexahydro-2,6-methano-1H-pyrrolizin-8-ylmethyl)-2-methoxybenzamide or a pharmaceutically acceptable salt thereof.

* * * * *

UNITED STATES PATENT AND TRADEMARK OFFICE
CERTIFICATE OF CORRECTION

PATENT NO. : 5,530,018   Page 1 of 3
DATED : June 25, 1996
INVENTOR(S) : Becker, et al.

It is certified that error appears in the above-identified patent and that said Letters Patent is hereby corrected as shown below:

Column 2, line 49, reading "991" should read --1991--.

Column 4, line 17, reading "methan1H" should read --methano-1H--.

Column 4, line 19 and Column 4, line 21, both instances reading "2,6methano" should read --2,6-methano--.

Column 4, line 23, reading "methano1H" should read --methano-1H--.

Column 4, line 55, reading "$C_1C_6$" should read --$C_1$-$C_6$--.

Column 6, line 19, reading "and/or $5-HT_4$" should read --and/or $5-HT_3$--.

Column 7, line 43 and Column 12, line 4, both instances reading "pyrrolizin8" should read --pyrrolizin-8--.

Column 7, line 44, reading "pyrrolizin8-ol 2" should read --pyrrolizin-8-ol-3--.

Column 7, line 55, reading "of primary" should read --of a primary--.

Column 7, line 58, reading "n is I" should read --n is 1--.

Column 7, line 64, reading "8methylamine and" should read --8-methylamine 8 and--.

Column 8, line 4, reading "hexahydro2,6" should read --hexahydro-2,6--.

UNITED STATES PATENT AND TRADEMARK OFFICE
CERTIFICATE OF CORRECTION

PATENT NO. : 5,530,018
DATED : June 25, 1996
INVENTOR(S) : Becker, et al.

It is certified that error appears in the above-identified patent and that said Letters Patent is hereby corrected as shown below:

Column 12, line 3, reading "Syn-4" should read --Syn-4---.

Column 13, line 8, reading "Cl:" should read --Cl: 363.1349--.

Column 15, line 20, reading "(C, 1)" should read --(C-1)--.

Column 16, line 2, reading "0,966" should read --0.966--.

Column 16, lines 5 and 8, both instances reading "0,073" should read --0.073--.

Column 16, line 52, reading "Cl:" should read --Cl: 377.1506--.

Column 17, lines 16 and 39, both instances reading "Cl:" should read --Cl: 335.1400--.

Column 18, line 2, reading "6.6" should read --66.6--.

Column 18, line 20, reading "2methoxy" should read --2-methoxy--.

Column 18, line 57, reading "prepared" should read --[prepared--.

Column 19, line 40, reading "Found: 152.1313" should read --Found: 152.1305--.

Column 20, line 6, reading "6.5" should read --56.5--.

UNITED STATES PATENT AND TRADEMARK OFFICE
CERTIFICATE OF CORRECTION

PATENT NO. : 5,530,018

DATED : June 25, 1996

INVENTOR(S) : Becker, et al.

It is certified that error appears in the above-identified patent and that said Letters Patent is hereby corrected as shown below:

Column 20, line 6, reading "38.0" should read --138.0--.

Column 20, line 35, reading "to give (3X)." should read --(3X).--.

Signed and Sealed this

Fifth Day of August, 1997

Attest:

BRUCE LEHMAN

Attesting Officer

Commissioner of Patents and Trademarks